US00PP37701P2

(12) United States Plant Patent
Monte-Michielsen

(10) Patent No.: US PP37,701 P2
(45) Date of Patent: Sep. 15, 2026

(54) GERANIUM PLANT NAMED 'TOSPL190415'

(50) Latin Name: ***Pelargonium* interspecific**
Varietal Denomination: TOSPL190415

(71) Applicant: Ball Horticultural Company, West Chicago, IL (US)

(72) Inventor: Fabienne Monte-Michielsen, Tinte (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 19/350,039

(22) Filed: Oct. 5, 2025

(51) Int. Cl.
*A01H 5/02* (2018.01)

(52) U.S. Cl.
USPC ..... Plt./324

(58) Field of Classification Search
USPC ..... Plt./324
CPC ..... A01H 6/425; A01H 5/02
See application file for complete search history.

*Primary Examiner* — Keith O. Robinson
(74) *Attorney, Agent, or Firm* — Megan Bowman

(57) ABSTRACT

A new and distinct cultivar of Geranium plant named 'TOSPL190415', characterized by its semi-double type, bright pink-purple-colored flowers, dark, green-colored foliage, and moderately vigorous, upright-mounded growth habit, is disclosed.

1 Drawing Sheet

Latin name of genus and species of plant claimed: *Pelargonium* interspecific.

Variety denomination: 'TOSPL190415'.

BACKGROUND OF THE INVENTION

The present invention relates to a new and distinct cultivar of Geranium plant botanically known as *Pelargonium* interspecific and hereinafter referred to by the cultivar name 'TOSPL190415'.

The new cultivar originated in a controlled breeding program in Hendrik-Ido-Ambacht, the Netherlands during June 2018. The objective of the breeding program was the development of Geranium cultivars that flower uniformly and have large flowers, dark, green-colored foliage, and a moderately vigorous, upright-mounded growth habit.

The new Geranium cultivar is the result of cross-pollination. The female (seed) parent of the new cultivar is proprietary *Pelargonium* interspecific breeding selection coded TB0277, not patented, characterized by its semi-double type, dark, pink-colored flowers, medium, green-colored foliage, and moderately vigorous, semi-upright growth habit. The male (pollen) parent of proprietary *Pelargonium* interspecific breeding selection coded TB2052, not patented, characterized by its semi-double type, medium purple-colored flowers, dark, green-colored foliage, moderately vigorous, spreading growth habit. The new cultivar was selected as a single flowering plant within the progeny of the above stated cross-pollination during July 2019 in a controlled environment in Hendrik-Ido-Ambacht, the Netherlands.

Asexual reproduction of the new cultivar by terminal stem cuttings since July 2019 in Hendrik-Ido-Ambacht, the Netherlands and Arroyo Grande, California has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'TOSPL190415' as a new and distinct cultivar of Geranium plant:

1. Semi-double type, bright pink-purple colored flowers;
2. Dark, green-colored foliage; and
3. Moderately vigorous, upright-mounded growth habit.

Plants of the new cultivar differ from plants of the female parent primarily in having dark, green-colored foliage. Plants of the new cultivar differ from plants of the male parent primarily in having an upright growth habit.

Of the many commercially available Geranium cultivars, the most similar in comparison to the new cultivar is FANTASIA Shocking Blue 'Tosfanshlu', U.S. Plant Pat. No. 33,377. However, in side-by-side comparisons, plants of the new cultivar differ from plants of 'Tosfanshlu' in at least the following characteristics:

1. Plants of the new cultivar have a flower color that has more pink coloration than flowers of plants of 'Tosfanshlu';
2. Plants of the new cultivar have more flowers per plant than plants of 'Tosfanshlu'; and
3. Plants of the new cultivar have leaves that are shorter in length than 'Tosfanshlu'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'TOSPL190415'. The approximately 15-week-old plants were grown in 6-inch pots approximately 5 weeks in a greenhouse in West Chicago, Illinois. Plants were not pinched.

DETAILED BOTANICAL DESCRIPTION

Figure 1:
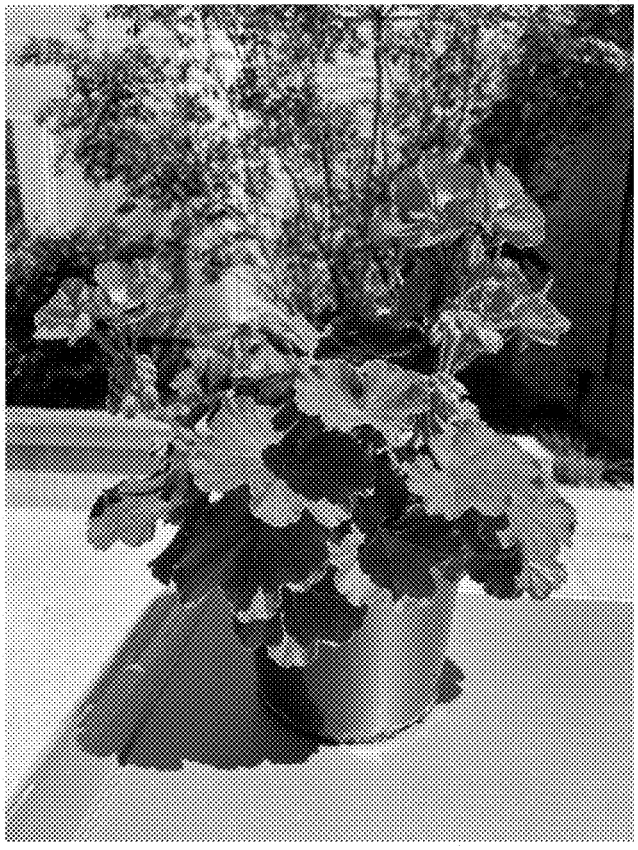
FIG. 1 illustrates a side view of the overall growth and flowering habit of 'TOSPL190415'.
Figure 2:
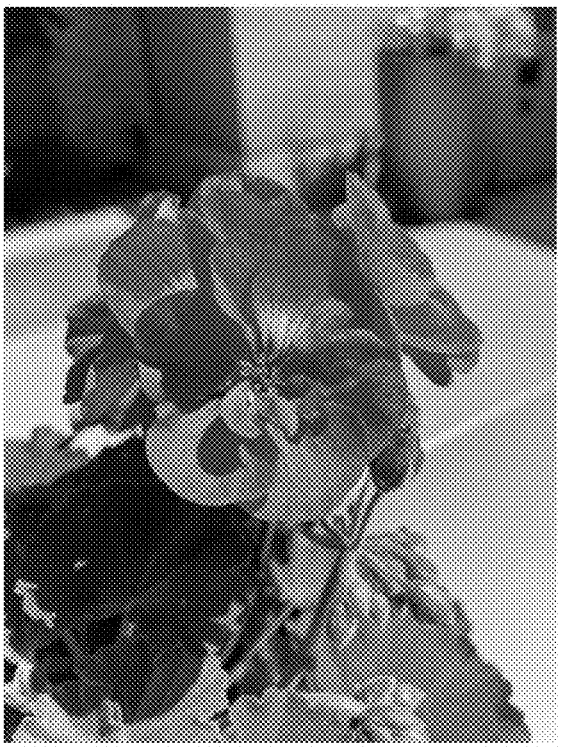
FIG. 2 illustrates a close-up view of an individual umbel of 'TOSPL190415'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in May 2025 under natural light conditions in West Chicago, Illinois.

The following descriptions and measurements describe approximately 15-week-old plants produced from cuttings from stock plants and grown in a double polyethylene greenhouse under conditions comparable to those used in commercial practice. The plants were grown in West Chicago, Illinois in 6-inch pots for approximately 5 weeks utilizing a soilless growth medium. Plants were not pinched. Greenhouse temperatures were maintained at approximately 65° F. to 70° F. (18.3° C. to 21.1° C.) during the day and approximately 60° F. to 65° F. (15.6° C. to 18.3° C.) during the night. Supplemental lighting was used. Measurements and numerical values represent averages of typical plants.

Botanical classification: *Pelargonium* interspecific 'TOSPL190415'.

Parentage:

*Female parent*.—Proprietary *Pelargonium* interspecific breeding selection coded TB0277, not patented.

*Male parent*.—Proprietary *Pelargonium* interspecific breeding selection coded TB2052, not patented.

Propagation:

*Type cutting*.—Terminal stem.

*Time to initiate roots*.—Approximately 9 to 12 days.

*Time to produce a rooted cutting*.—Approximately 21 to 28 days.

*Root description*.—Fibrous.

*Rooting habit*.—Freely branching.

Plant description:

*Commercial crop time*.—Approximately 8 to 9 weeks from a rooted cutting to finish in a 10 cm pot.

*Growth habit and general appearance*.—Moderately vigorous, upright-mounded.

*Size*.—Height from soil level to top of plant plane: Approximately 21.0 cm. Height from soil level to top of foliage: Approximately 13.0 cm. Width: Approximately 28.0 cm.

*Branching habit*.—Freely basal branching, pinching enhances basal branching. Quantity of main branches per plant: Approximately 3.

*Branch*.—Strength: Strong. Length: Approximately 12.0 cm. Diameter: Approximately 7.0 mm. Length of central internode: Approximately 1.5 cm. Texture: Densely pubescent with a mixture of glandular and nonglandular hairs. Gland color: Colorless, transparent. Color of young and mature stems: 143C.

Foliage description:

*General description*.—Quantity of leaves per branch: Approximately 10. Fragrance: Slight, mildly herbal. Form: Simple. Arrangement: Opposite.

*Leaves*.—Aspect: Petiole is at an acute angle to stem; blade is perpendicular to stem. Shape: Reniform. Margin: Bicrenate, palmately lobed, somewhat wavy. Apex: Obtuse. Base: Cordate. Venation pattern: Palmate. Length of mature leaf: Approximately 6.5 cm. Width of mature leaf: Approximately 7.5 cm. Texture of upper and lower surfaces: Densely pubescent with a mixture of glandular and nonglandular hairs. Gland color: Colorless, transparent. Color of upper surface of young foliage: Closest to 137B venation of 144B. Color of lower surface of young foliage: Closest to 147C with venation of 146C. Color of upper surface of mature foliage: Closest to NN137B with venation of 146B, no zonation observed. Color of lower surface of mature foliage: Closest to 147B with venation of 146B.

*Petiole*.—Length: Approximately 5.5 to 6.5 cm. Diameter: Approximately 2.5 mm. Texture: Densely pubescent with a mixture of glandular and nonglandular hairs. Gland color: Colorless, transparent. Color: 144A.

Flowering description:

*Flowering habit*.—'TOSPL190415' is freely flowering under outdoor growing conditions with substantially continuous blooming from spring through autumn and year-round in greenhouse environment.

*Lastingness of individual flower on the plant*.—Approximately 12 to 14 days.

Inflorescence description:

*General description*.—Type: Umbel, semi-spherical. Positioned above foliage. Quantity of fully open umbels per plant: Approximately 5 to 6. Quantity of developing umbels per plant: Approximately: 2. Fragrance: Slight, mildly herbal. Length or height: Approximately 5.0 cm. Width: Approximately 8.0 cm. Quantity of fully open flowers per inflorescence: Approximately 8.

*Peduncle*.—Strength: Strong. Aspect: Erect. Length: Approximately 12 cm. Diameter: Approximately 3.0 mm. Texture: Densely pubescent with a mixture of glandular and nonglandular hairs. Gland color: Colorless, transparent. Color: 144A with an overlay of 187B.

Flower description:

*General description*.—Type: Semi-double.

*Bud*.—Rate of opening: Generally, takes 3 to 4 days for bud to progress from first color to fully open flower.

*Bud just before opening*.—Shape: Elliptic. Length: Approximately 1.4 cm. Width: Approximately 0.8 mm. Sepal texture: Densely pubescent with a mixture of glandular and nonglandular hairs. Gland color: Colorless, transparent. Petal texture: Glabrous. Petal color: NN74A.

*Corolla*.—Shape: Round. Diameter: Approximately 5.0 cm. Depth: Approximately 1.5 cm.

*Petals*.—Quantity: Approximately 6 to 8 petals. Shape: Obovate. Appearance: Matte. Margin: Entire. Apex: Obtuse to slightly notched. Base: Attenuate. Length of upper petals: Approximately 2.0 cm. Width of upper petals: Approximately 1.7 cm. Length of lower petals: Approximately 2.5 cm. Width of lower petals: Approximately 2.6 cm. Texture of upper and lower surfaces: Glabrous. Color of upper surface of upper petals when fully open: Closest to N74A with N155B at base. Color of lower surface of upper petals when fully open: 72C with venation of 67B at base. Color of upper surface of lower petals when fully open: Closest to N74B to N155B at base with venation of N74B. Color of lower surface of lower petals when fully open: 66D with venation of 67A at base.

*Calyx*.—Shape: 5-pointed star. Diameter: Approximately 2.0 cm.

*Sepals*.—Quantity per flower: Approximately 5, fused at base. Shape: Lanceolate. Margin: Entire. Apex: Acuminate. Length of upper sepal: Approximately 1.1 cm. Width of upper sepal: Approximately 3.5 mm. Length of lower sepals: Approximately 1.0 cm. Width of lower sepals: Approximately 2.0 mm. Texture of upper surface: Glabrous. Texture of lower surface: Densely pubescent with a mixture of glandular and nonglandular hairs. Gland color: Colorless, transparent. Color of upper surface: 143A with a faint overlay of 185B at base. Color of lower surface: 143A with an overlay of 185A at base.

*Pedicel*.—Strength: Strong. Aspect: Acute angle to peduncle. Length: Approximately 2.0 cm. Diameter: Approximately 1.5 mm. Texture: Densely pubescent with a mixture of glandular and nonglandular hairs. Gland color: Colorless, transparent. Color: 146B with a heavy overlay of 187A.

*Reproductive organs*.—Androecium: Quantity of mature stamens: Approximately 10 per flower. Anther shape: Oblong. Anther length: Approximately 2.0 mm. Anther color: Closest to NN78A. Filament length: Approximately 7.0 mm. Filament color: NN155D tinted with N78A nearest anther. Pollen amount: None detected. Gynoecium: Pistil quantity: 1 per flower. Pistil length: Approximately 9.0 mm. Stigma shape: 5 branched. Stigma length: Approximately 2.0 mm. Stigma color: 71A. Style length: Approximately 3.0 mm. Style color: Closest to 71B. Ovary length: Approximately 4.0 mm. Ovary texture: Densely pubescent. Ovary color: 144A with an overlay of 71A.

Seed and fruit production: Neither seed nor fruit production has been observed.

Disease and pest resistance: Resistance to pathogens and pests common to Geranium has not been observed.

What is claimed is:

1. A new and distinct cultivar of Geranium plant named 'TOSPL190415', substantially as herein illustrated and described.

* * * * *